United States Patent
Béduer et al.

(10) Patent No.: US 11,724,006 B2
(45) Date of Patent: Aug. 15, 2023

(54) CRYOGEL 3D SCAFFOLDS AND METHODS FOR PRODUCING THEREOF

(71) Applicant: ECOLE POLYTECHNIQUE FEDERALE DE LAUSANNE (EPFL), Lausanne (CH)

(72) Inventors: Amélie Barbara Hildegarde Béduer, Lausanne (CH); Thomas Braschler, Chavannes-Renens (CH); Philippe Renaud, Préverenges (CH)

(73) Assignee: École Polytechnique Fédérale de Lausanne (EPFL), Lausanne (CH)

( * ) Notice: Subject to any disclaimer, the term of this patent is extended or adjusted under 35 U.S.C. 154(b) by 1041 days.

(21) Appl. No.: 16/476,564

(22) PCT Filed: Jan. 10, 2018

(86) PCT No.: PCT/IB2018/050149
§ 371 (c)(1),
(2) Date: Jul. 9, 2019

(87) PCT Pub. No.: WO2018/130949
PCT Pub. Date: Jul. 19, 2018

(65) Prior Publication Data
US 2019/0336649 A1    Nov. 7, 2019

(30) Foreign Application Priority Data
Jan. 10, 2017  (GB) ..................... 1700368

(51) Int. Cl.
*A61L 27/52*     (2006.01)
*B33Y 10/00*     (2015.01)
*B33Y 70/00*     (2020.01)
*B33Y 80/00*     (2015.01)
*B29C 64/112*    (2017.01)
*B29C 64/245*    (2017.01)
*A61L 27/56*     (2006.01)
*B29C 64/00*     (2017.01)
*B29C 35/16*     (2006.01)
*C12M 1/00*      (2006.01)
*C12M 1/12*      (2006.01)
*B29K 105/00*    (2006.01)
*B29L 31/00*     (2006.01)

(52) U.S. Cl.
CPC .............. *A61L 27/52* (2013.01); *A61L 27/56* (2013.01); *B29C 35/16* (2013.01); *B29C 64/00* (2017.08); *B29C 64/112* (2017.08); *B29C 64/245* (2017.08); *B33Y 10/00* (2014.12); *B33Y 70/00* (2014.12); *B33Y 80/00* (2014.12); *C12M 1/12* (2013.01); *C12M 23/34* (2013.01); *C12M 25/14* (2013.01); *A61L 2400/06* (2013.01); *B29K 2105/0002* (2013.01); *B29K 2105/0061* (2013.01); *B29L 2031/7532* (2013.01)

(58) Field of Classification Search
CPC ...... A61L 27/52; A61L 27/56; A61L 2400/06; B29C 35/16; B29C 64/00; B29C 64/112; B29C 64/245; B29C 64/106; B33Y 10/00; B33Y 70/00; B33Y 80/00; B33Y 50/02; C12M 1/12; C12M 23/34; C12M 25/14; C12M 33/00; B29K 2105/0002; B29K 2105/0061; B29L 2031/7532
See application file for complete search history.

(56) References Cited

U.S. PATENT DOCUMENTS

| | | | |
|---|---|---|---|
| 6,103,255 A * | 8/2000 | Levene | ............... A61L 27/3839 521/64 |
| 2010/0291176 A1 | 11/2010 | Chian et al. | |
| 2014/0112973 A1* | 4/2014 | Steinberg | ................ A61L 31/16 424/443 |
| 2022/0133465 A1* | 5/2022 | Rocco | .................... A61L 27/48 600/37 |

FOREIGN PATENT DOCUMENTS

| | | | |
|---|---|---|---|
| CN | 103057123 A | | 4/2013 |
| CN | 104307047 A | | 1/2015 |
| KR | 101541249 B1 | * | 8/2015 |
| RU | 2015144535 A | | 3/2016 |
| WO | 2008069761 A1 | | 6/2008 |

OTHER PUBLICATIONS

T.H. Petersen et al. "Tissue-Engineered Lungs for in Vivo Implantation," Science, Jul. 30, 2010, pp. 538-541, vol. 329 issue 5991, American Association for the Advancement of Science, USA; Cited in Specification.

(Continued)

*Primary Examiner* — Titilayo Moloye
(74) *Attorney, Agent, or Firm* — Pabst Patent Group LLP

(57) ABSTRACT

A method of producing a cryogel-based multicompartment 3D scaffold is herein disclosed. The method comprises the steps of: a) providing a first frozen polymeric layer on a refrigerated support kept at subzero temperature; b) providing subsequent polymeric layers to obtain a stack of polymeric layers by possibly modulating the subzero temperature of the refrigerated support; c) optionally incubating the final polymeric structure at subzero temperature; and d) placing the produced cryogel at a temperature above 0° C., the method being characterized in that each subsequent layer i) is deposited on the previous one after freezing of this latter; ii) is deposited on the previous one before the complete polymerization of this latter; and iii) is deposited with a temperature higher than the freezing temperature of the previously deposited layer. Cryogel scaffolds obtained from the method of the invention are also disclosed.

18 Claims, 9 Drawing Sheets

(56) References Cited

OTHER PUBLICATIONS

S. Zhou et al. "Ion-responsive alginate based macroporous injectable hydrogel scaffolds prepared by emulsion templating," Journal of Materials Chemistry B, Oct. 7, 2013, pp. 4736-4745, vol. 1 issue 37, Royal Society of Chemistry, United Kingdom; Cited in Specification.
A.J. Thornton et al. "Shape-Defining Scaffolds for Minimally Invasive Tissue Engineering," Transplantation, Jun. 27, 2004, p. 1798-1803, vol. 77 issue 12, Lippincott Williams & Wilkins, USA; Cited in Specification.
S.A. Bencherif et al. "Injectable preformed scaffolds with shape-memory properties," Proceedings of the National Academy of Sciences of the United States of America, 27, Nov. 2012, pp. 19590-19595, vol. 109 issue 48, PNAS, USA; Cited in Specification.
A. Béduer et al. "A Compressible Scaffold for Minimally Invasive Delivery of Large Intact Neuronal Networks," Advanced Healthcare Materials, Sep. 1, 2014, pp. 301-312, vol. 4 issue 2, Wiley, USA; Cited in Specification.
H.J. Yen et al. "Fabrication of Precision Scaffolds Using Liquid-Frozen Deposition Manufacturing for Cartilage Tissue Engineering," Tissue Engineering Part A, May 2009, pp. 965-975, vol. 15 No. 5, Mary Ann Liebert, Inc., USA; Cited in Specification.
Y. Yan et al. "Layered manufacturing of tissue engineering scaffolds via multi-nozzle deposition," Materials Letters, 2003, pp. 2623-2628, vol. 57, Elsevier Science B.V., The Netherlands; Cited in ISR.
International Search Report dated Feb. 5, 2018 filed in PCT/IB2018/050149.
Office Action dated Jul. 10, 2017 issued in United Kingdom priority application No. GB1700368.2.

* cited by examiner

CRYOGEL 3D SCAFFOLDS AND METHODS FOR PRODUCING THEREOF

TECHNICAL FIELD

The invention lies in the field of manufacturing methods for biological scaffolds.

BACKGROUND ART

The design of 3D scaffolds capable to support, instruct and guide cells both in vitro and in vivo is one of the major focus areas of tissue engineering. 3D structures can be produced by a number of methods, including casting, stereo- and photolithography, and additive manufacturing (3D-printing). Particularly with the rapid evolution of 3D printers, additive manufacturing of combinations of biomaterials and cells with the aim to ultimately print entire organs has become a mainstream approach.

3D scaffold manufacture generally requires the use of a polymeric, biological or biomimetic scaffolding material. Fundamentally, cells can either be present during manufacture, or seeded at a later point of time, the mainstream approach being to mix cells directly with scaffold precursors, particularly in 3D printing approaches. This provides control over the cell position due to gel formation after printing, and at the same time provides the necessary cell adhesion. The primary reason for printing cells and materials simultaneously is that it is difficult to seed cells with sufficient spatial control, and sufficient depth into finished scaffolds. This approach has nevertheless a few very important disadvantages. First, the presence of cells during the manufacturing process implies the need for a sterile environment on the one hand, and protection of operating personnel against possible biohazards on the other, both driving cost especially in a clinical setting. Second, when cells and scaffolds are printed at the same time, the materials used for the scaffold are not sufficiently porous. As a consequence, upon implantation, vascularization is slowed down by the lack of porosity, even in biodegradable materials. As a response to these disadvantages, technologies allowing the creation of porous scaffolds are being developed, primarily by the use of sacrificial materials. Such scaffolds address the need for porosity and, once the sacrificial material (e.g. an ink) is removed, allow for a posteriori seeding.

3D manufacturing should not only aim at controlling the structure of the biomatrix, but ideally also the spatial distribution of cells there within. When seeding cells into an otherwise finished porous scaffolds, alternative cell positioning strategies need to be found. Experiments with scaffolds derived by decellularization of entire organs show that it is indeed possible to obtain functional organs by seeding of cell mixtures into porous, initially cell-free construct. In the lung, for instance, it has been shown that it is enough to seed compartment-wise: when a mix of pulmonary epithelial cells (airway cells) is seeded onto a decellularized lung scaffold through the airways, and a mix of vascular cells through the pulmonary vascular scaffold, the instructions contained in the cell-free matrix are sufficient to allow for spatial organization of functional cell types, and ultimately the development of a new, minimally functional lung (Petersen, T. H. et al., Science 30 Jul 2010, Vol. 329, Issue 5991, pp. 538-541).

Moreover, in the tissue engineering field, the use of a smart cellular scaffold systems which are highly and reversibly compressible for minimally invasive implantation procedure, is highly desired. To achieve this goal, several requirements must be met: the scaffold must be highly compressible, such that mL-scale volumes can be delivered through narrow-bore tubing or needles, yet it should recover its original shape, volume and organization quickly after the injection process; it should preserve cells' integrity and morphology during the compression associated with the delivery process, but nevertheless behave as a globally soft material to minimize scarring reactions; further, for the long-term culture necessary to develop networks of differentiated cells and the potential clinical translation, the scaffolds need to be reliably sterilized, preferentially by autoclaving. Macroporous scaffolds with such a shape memory behaviour can be fabricated by different techniques, such as emulsion polymerization, lyophilization, and cryogelation. (S. Zhou et al., J. Mater. Chem. B 2013, 1, 4736; A. J. Thornton et al., Transplantation 2004, 77, 1798; S. A. Bencherif et al., Proc. Natl. Acad. Sci. U.S.A. 2012, 109, 19590). This latter in particular involves polymerization of a hydrogel precursor at subzero temperature, and produces particularly robust, reversibly compressible gels, which can for instance be used for minimally invasive delivery (S. A. Bencherif et al., Proc. Natl. Acad. Sci. U.S.A. 2012, 109, 19590).

Chinese patent application CN 103057123 describes a three-dimensional printing system comprising a three-dimensional model design work station and a three-dimensional printing machine having a printing head, an ink box and a printing platform. The system is characterized in that the printing platform is provided with a refrigerating device. The system and the method for using thereof are particularly suitable for preparing nerve regeneration implant based on various types of extracellular matrix molecules as well as polysaccharides molecule supports in the form of a cryogel, and can accurately control the forms and corresponding parameters of the supports. However, the described method does not provide any hint on how to provide a multicompartment cryogel scaffold having in-built areas of different structural features, such as different porosity, in order to control the post-process spatial distribution of cells upon seeding thereof within the final scaffold. It also does not provide a means to obtain sufficiently robust and compressible gels to allow for minimally invasive delivery.

SUMMARY OF INVENTION

Bearing in mind all the drawbacks of the prior art, and in order to tackle and overcome them, the present inventors developed a method exploiting an additive manufacturing approach for producing compressible cryogel scaffolds. The obtained scaffolds combine free form-design with minimally invasive delivery through syringe needles or other narrow-bore tubing, without loss of cell viability in the case of cells transplanted. By printing cell-free hydrogel inks onto a freezing cold stage, and making use of cryogelation technology, the inventors proved able to obtain a 3D porous scaffolds with extreme porosity and quick reversible compressibility (i.e. recovery of up to 99.9% of the initial shape within 1 minute after compression and release) that can then be further easily sterilized. They can be deeply seeded with cells due to their highly interconnected pore structure, for instance by exploiting a compression/rehydration cycle to draw a cell suspension into the pore space. For minimally invasive delivery, the scaffolds can be compressed and partially dehydrated once more, before delivery through narrow-bore conduits followed by regain of shape and volume.

Most importantly, organization can be generated inside the scaffold during the manufacturing process: areas of the scaffold can be structured with small pores and other neighbouring areas with large pores, or no porosity, and any combination of thereof. The differences in porosity can come from a difference of the temperature used for the manufacturing of the different scaffolds areas. In the case of cryogels, temperatures below 0° C. will lead to porous areas. The further below the freezing point the temperature of manufacturing is, the lower is the resulting pores size. However, if the temperature is higher than the freezing temperature, the resulting areas of the scaffold will not be porous (at the microscopic scale, there will still be the intrinsic porosity of hydrogels which is typically in the range of a few nanometers to a few hundred nanometers).

In one embodiment of the proposed method, a 3D printing approach has been taken, which makes use of a particular sacrificial material for 3D printing: water ice. Indeed, when printing onto a cold stage, water-based printing inks will rapidly freeze. If the ink contains a suitable prepolymer mixture, a sponge-like cryogel will forms in the process. The pore size can be controlled from less than 1 µm (not accessible to cells) to a few hundred micrometers (accessible to cells in vitro and also to vascularization in-vivo). This is done by controlling the freezing rate, which in turn is controlled by the temperature of the printing stage. In-vivo, the porosity translates into rapid vascularization upon implantation.

While 3D printing allows for extensive freedom in terms of geometry, it is by no means the only way the invention can be applied. It is for instance possible to perform successive casting steps with molds of different shapes, or to use screen printing or stereolithography for the successive layers.

Moreover, the presently invented method provides proof of principle for the production in a single step of built-in compartments in a fully 3D printed scaffold. By modulating the temperature of the support wherein the scaffold is printed, and tailoring the printing/dispensing time of bioinks and water (used optionally as sacrificial material for very large pore formation), a plurality of compartments with different structural characteristics can be easily obtained. As a consequence, thanks to areas of different pore size, cells are allowed to reach only defined compartment by flow through the scaffolds upon seeding thereon.

The key technical challenge of the invention was to obtain said compartments being mechanically bound to one another so to guarantee the functionality of the final scaffold. To this aim, it is necessary to appropriately control the polymerization and freezing rates. Indeed, cryogels with sufficient robustness for minimally invasive delivery by partial dehydration (compression to remove pore fluid) are obtained if the polymerization occurs primarily in the cold, semi-frozen state with ice crystals and a concentrated polymer solution between them (A. Beduer, T. Braschler et al., Adv. Healthc. Mater. 2015 Jan. 28; 4(2):301-12).

For the strong adhesion between successive layers and the different compartments, it is necessary that a strong material connection be established between them. For this, the following conditions need to be met: first, the polymerization should not be completed before the deposition of the adjacent compartment, drop, or layer. Second, intimate contact needs to occur between the new material and the already frozen one. This is best realized by local re-melting of the surface by using ink substantially above the freezing temperature. Third, no or minimal undue water (ice or liquid) should be present at the interface before deposition of the subsequent layer, in order to avoid physical separation or formation of a mechanically weak zone (due to substantial local dilution of the bio-ink).

To enable crosslinking between already deposited, typically frozen material, and the next layer, drop, or compartment, it is necessary that chemical bond formation between the old and new material occurs. For this, the polymerization of the previously deposed material needs to be incomplete upon arrival of the new material. This in turn can for instance be achieved through appropriate control of the reaction kinetics, such that polymerization in the already deposited material is incomplete upon arrival of new adjacent material.

In a two component reaction system, there is in addition the possibility to use non-stoichiometric amounts of the two reaction partners, such that functional groups remain permanently available. A combination of sufficiently slow reaction kinetics and stoichiometric mismatch can advantageously be used.

Undue water ice or liquid deposition at the interfaces prior to deposition of the adjacent material occurs primarily through condensation from air humidity, and can therefore be reduced by controlling air humidity, by providing a temporary protective layer (in particular when using molding techniques), or, albeit incompletely, by sufficiently fast printing.

Finally, since reversible compressibility and mechanical ruggedness for minimally invasive delivery through narrow bore conduits are generally linked to polymerization primarily in the semi-frozen state (A. Beduer, T. Braschler et al., Adv. Healthc. Mater. 2015 Jan. 28; 4(2):301-12; S. A. Bencherif et al., Proc. Natl. Acad. Sci. U.S.A. 2012, 109, 19590), the reaction rate should still be chosen sufficiently rapid to allow for cryogel formation in a useful cryo-incubation period (typically, below a year, preferably below 1 month, and even more preferably less than a week).

Accordingly, it is an object of the present invention to provide for

A method of producing a cryogel-based multicompartment three-dimensional scaffold, said method being characterized in that it comprises the steps of:

a) providing a first frozen polymeric layer on a refrigerated support kept at subzero temperature;

b) providing subsequent polymeric layers to obtain a stack of polymeric layers by possibly modulating the subzero temperature of the refrigerated support;

c) optionally incubating the final polymeric structure at subzero temperature; and d) placing the produced cryogel at a temperature above 0° C. the method being characterized in that each subsequent layer:

i) is deposited on the previous one after freezing of this latter;

ii) is deposited on the previous one before the complete polymerization of this latter; and iii) is deposited with a temperature higher than the freezing temperature of the previously deposited layer.

In one embodiment, the method is characterized in that providing a first frozen polymeric layer of step a) comprises the steps of:

a') depositing at least a liquid precursor of at least a polymeric material on a refrigerated support kept at subzero temperature to form a first polymeric layer; and a") allowing said first polymeric layer to freeze to form a first frozen polymeric layer.

In one embodiment, the method is characterized in that step b) is performed by casting and molding, 3D printing, screen printing or photopolymerization of at least a liquid precursor of at least a polymeric material, as well as combinations of the foregoing.

In a particular embodiment, step b) of the method is performed by 3D printing. In this embodiment, the method further comprises the steps of:

x) obtaining a software-based 3D model of the three-dimensional scaffold on a computer;)

xx) operatively connecting said computer to a 3D printer having at least one biomaterial-based ink cartridge and a water cartridge; and xxx) printing layers of the cryogel according to the software-based 3D model by dispensing the content of the cartridges on a refrigerated support kept at subzero temperature.

In a particular embodiment, the method is characterized in that voids present in the 3D scaffold are obtained by using the water of the water cartridge.

In a particular embodiment, the method is characterized in that the temperature of the refrigerated support of the 3D printer is controlled and regulated by the computer running the software-based 3D model of the 3D scaffold, and according to said 3D model.

In one embodiment, the method is characterized in that the temperature of the refrigerated support is modulated over time so that each layer defines a scaffold compartment.

In one embodiment, the method is characterized in that the temperature of the refrigerated support is modulated over time so that each layer can define more than one scaffold compartment.

In one embodiment, the method is characterized in that the temperature of the refrigerated support is modulated along the support so that each layer can define more than one scaffold compartment.

In one embodiment, the method is characterized in that the temperature modulation is performed by steps of 10° C.

In one embodiment, the method is characterized in that the temperature modulation is performed continuously.

In one embodiment, the method is characterized in that the temperature modulation is performed using a predefined set of levels of temperatures (e.g: −20° C. and −80° C.).

In one embodiment, the method is characterized in that the refrigerated support is a plate, a chamber or a reservoir.

In one embodiment, the method is characterized in that the polymeric material comprises a natural polymeric material such as extracellular matrix-derived polymeric material, a synthetic polymeric material or combinations thereof.

In one embodiment, the method is characterized in that the temperature of the refrigerated support is comprised between the freezing point of the polymeric material and absolute zero, preferably between 0° and −200° C., even more preferably between −20° and −80° C. for water-based polymeric materials.

In one embodiment, the method is characterized in that the polymeric material does not comprise any cross-linker.

A further object of the present invention relates to a cryogel-based multicompartment three-dimensional scaffold obtainable by the method of the invention, characterized in that it comprises a stack of layers mechanically connected among them by a built-in, intermediate thin layer.

In one embodiment, the scaffold is characterized in that it is reversibly compressible so that it regains up to 99% of its shape after compression and release within one minute.

In one embodiment, the scaffold is characterized in that it has a network of interconnected pores with a porosity comprised between 50% and 99%.

In one embodiment, the scaffold is characterized in that it comprises small-pore compartments separated from large-pore compartments, wherein the ratio of average large-pore diameter to small-pore diameter is of at least 2, preferably of at least 5.

In one embodiment, a built-in, intermediate thin layer has a pore size sufficiently small such as to act as a barrier to living cells between adjacent layers with larger pore size.

In one embodiment, the scaffold is characterized in that it has a mean pore size comprised between 1 µm and 10 mm, preferably between 1 µm and 5 mm, more preferably between 1 µm and 2 mm, even more preferably between 5 µm and 500 µm.

In one embodiment, the scaffold is characterized in that the pore volume/pore's walls thickness ratio of the scaffold is of at least 5, preferably above 10.

In one embodiment, the scaffold is characterized in that the reversible compressibility volume ratio between hydrated and dehydrated state is comprised between 1.2 and 50, preferably between 2 to 15.

In one embodiment, the scaffold is characterized in that the reversible compressibility volume ratio between hydrated and dry state is comprised between 2 and 1000.

In one embodiment, the scaffold is characterized in that the overall mass of dry material content of the scaffold is comprised between 0.1% and 10%, preferably between 0.5% and 3%.

In one embodiment, the scaffold is characterized in that it is flowable and injectable through a syringe needle.

In one embodiment, the scaffold is characterized in that it comprises an active compound therein and/or thereon.

BRIEF DESCRIPTION OF THE DRAWINGS

In the Figures

DESCRIPTION OF EMBODIMENTS

Figure 1:
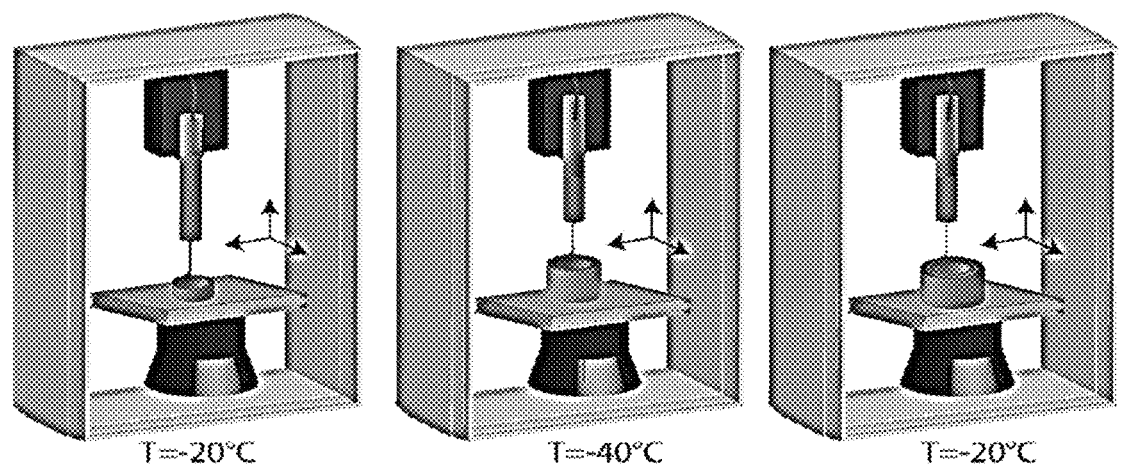
FIG. 1 shows an embodiment of the method of the invention using a 3D printing approach for creating a 3D structured scaffold made of two different materials and water as sacrificial material.
Figure 1:
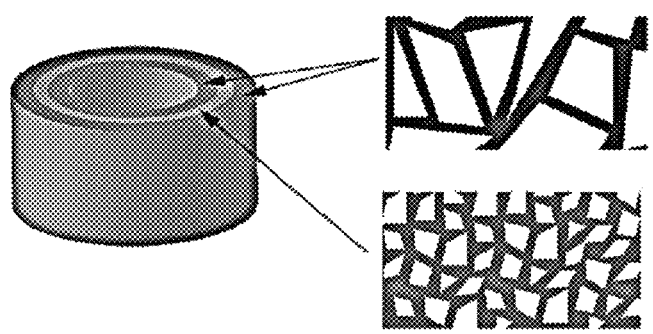

The present disclosure may be more readily understood by reference to the following detailed description presented in connection with the accompanying drawing figures, which form a part of this disclosure. It is to be understood that this disclosure is not limited to the specific conditions or parameters described and/or shown herein, and that the terminology used herein is for the purpose of describing particular embodiments by way of example only and is not intended to be limiting of the claimed disclosure.

As used herein and in the appended claims, the singular forms "a", "an" and "the" include plural referents unless the context clearly dictates otherwise. Thus, for example, reference to "a cartridge" includes a plurality of such cartridges and reference to "a compartment" includes reference to one or more compartments, and so forth.

Also, the use of "or" means "and/or" unless otherwise stated. Similarly, "comprise", "comprises", "comprising", "include", "includes", and "including" are interchangeable and not intended to be limiting. It is to be further understood that where descriptions of various embodiments use the term "comprising", those skilled in the art would understand that in some specific instances, an embodiment can be alternatively described using language "consisting essentially of" or "consisting of."

The present invention provides for a method of producing a cryogel-based multicompartment three-dimensional scaffold. Cryogels, for use in the fields of tissue engineering and regenerative medicine, are gaining increased interest due to their inherent interconnected macroporous structure and ease of formation in comparison to other macropore forming techniques. Cryogelation is a simple method that avoids the need for porogen removal and forms inherently interconnected scaffolds. Cryogels, characteristically sponge-like macroporous hydrogels formed at temperatures below the freezing point of the solvent (typically water, although cryogels from suitable monomers can also be fabricated using organic solvents), avoid concerns such as cytotoxicity by utilizing frozen solvent crystals as the interconnecting porogen. Porogen removal is achieved by simply holding the cryogel at temperatures above the solvent freezing point. Typically, the gel solution is cooled below the freezing point. At these temperatures, a large percentage of the solvent crystallizes; however, a portion of the gel solution is maintained in its liquid form. As the solvent crystallizes, the hydrogel constituents are concentrated in liquid microphases, rather than preserved in the crystallized macrophase. The concentration of the hydrogel monomers, oligomers, or polymers is known as cryoconcentration and accelerates the rate of gel formation. After a suitable gelation period, the cryogel is returned to room temperature. As the solvent crystals melt, hydrating the network, an interconnected macroporous hydrogel structure is formed. For tissue engineering applications, it is desirable that the pores within hydrogels are highly interconnected to allow for the migration and proliferation of cells and to limit regions of inaccessibility. The necessity for pore interconnectivity highlights a significant advantage of the cryogel technique over other pore-forming techniques, as cryogels are inherently highly interconnected (open-celled gels). During solvent crystallization, solvent crystals grow until the leading edge comes into contact with another crystal front, resulting in highly interconnected porous gels.

An advantage of cryogels compared to e.g. conventional macroporous hydrogels obtained by phase separation is their high mechanical stability. They are very tough, and can withstand high levels of deformations, primarily compression, but also some elongation and torsion; they can in particular be squeezed under mechanical force to drain out their solvent content.

In the application of cryogels in tissue engineering and as a cell support construct, there is a focus on naturally occurring materials such as chitosan, alginate, gelatin, and collagen, due to their biocompatible nature and the existence of well-documented crosslinking methods. Cryogels have been and continue to be investigated for a number of bio-related applications, including bioseparation, biocatalysis, chromatography, monolayer cell proliferation, and more recently, regenerative medicine. Cryogel scaffolds have the potential to be utilized in a wide range of tissue engineering applications, reaching from cartilage to neural tissue repair. Due to the cryoconcentration of polymers, cryogels generate very robust porous sponge-like gels, which makes them appropriate scaffolds for e.g. cartilage and non-load bearing bone applications. Thus, cryogel scaffolds have the potential to be utilized for a wide range of tissue engineering applications.

The method of the invention comprises the steps of:

a) providing a first frozen polymeric layer on a refrigerated support kept at subzero temperature;

b) providing subsequent polymeric layers to obtain a stack of polymeric layers by possibly modulating the subzero temperature of the refrigerated support;

c) optionally incubating the final polymeric structure at subzero temperature; and d) placing the produced cryogel at a temperature above 0° C.

the method being characterized in that each subsequent layer:

i) is deposited on the previous one after freezing of this latter;

ii) is deposited on the previous one before the complete polymerization of this latter; and iii) is deposited with a temperature higher than the freezing temperature of the previously deposited layer.

In one embodiment, step b) is performed by casting and molding, 3D printing, screen printing or photopolymerization of at least a liquid precursor of at least a polymeric material, as well as combinations of the foregoing.

In one embodiment, step a) is replaced by the steps of:

a') depositing at least a liquid precursor of at least a polymeric material on a refrigerated support kept at subzero temperature to form a first polymeric layer; and a") allowing said first polymeric layer to freeze to form a first frozen polymeric layer.

The method of producing a scaffold according to the invention foresees, among others, the use of a 3D printing approach. 3D printing is emerging as a complex tissue manufacturing technique, and offers great precision to control the internal architecture of a scaffold and print complicated structures close in architecture to native tissue. Based on computer-aided design (CAD) models, 3D printers can fabricate a predesigned patient-specific tissue construct in a layer-by-layer fashion. Furthermore, non-invasive imaging techniques of patients' tissues or defects can be obtained and used to inform CAD design, which would allow the scaffold to be a specifically sized implant perfectly fitting into the defect site.

3D printing and rapid prototyping processes have been used to create scaffolds that are 3D with user defined micro-structures and micro-scaled architectures, allowing full control over the distribution and size of pores and wall material in nearly arbitrary geometries. This ensures that a great many more complex, predesigned architectures patterns and structures can be implemented. Both for hard and soft tissues, interconnected pores, specific pore structures at the micro-scale, and interconnections are very important for the scaffold design. A complicated, hierarchical structure is one that is difficult to replicate, and is more difficult to control with other common scaffold fabrication techniques. With the application of 3D printing, there is an allowance not only for the creation of delicate and intricate structures from the advanced working of strong and robust materials, but the potential to create highly ordered structures that could conceivably match any desired architecture.

However, all 3D printing processes offer advantages and disadvantages. The type of 3D printer chosen for an application often depends on the materials to be used and how the layers in the finished product are bonded. The three most commonly used 3D printer technologies in medical applications are selective laser sintering (SLS), thermal inkjet (TIJ) printing, and fused deposition modeling (FDM). The main feature of these systems is their ability print cell-laden gels to yield viable and functional scaffolds. The printers utilize a pneumatic pressurized system to extrude the material from "bioink" cartridges, comprising the biological material of choice. The disadvantage of using these systems are usually the shear stress from the variously sized nozzles, which may negatively impact cell viability during the printing process, the need to often add synthetic polymers to improve the mechanical features of natural polymers (with possible biocompatibility or safety issues), the need to include further manufacturing steps such as the addition of electrospinning to 3D printing and the high temperature which risk to kill the cells, denaturate/alter the biological materials and impede the correct formation of the required scaffold architecture. For instance, the types of biomaterials that can be applied in the FDM process are usually restricted to thermoplastic or thermally stable materials. The high temperature in the conventional FDM process can result in polymer chain scission and degradation, and the scaffolds can easily lose mechanical strength.

A method called liquid-frozen deposition manufacturing (LFDM), based on a non-heating process, was developed by Yen H. J. and colleagues (Tissue Eng Part A. 2009 May; 15 (5): 965-75), that allows to handle many polymers that are susceptible to thermal hydrolysis. The material ejected by the output nozzle is frozen and deposited layer by layer on a low-temperature platform to form a precise structure in a designed shape. However, this system and method does not enable to fine tuning the porosity of the formed scaffold.

In view of all these drawbacks, in one aspect the present invention relates to a novel method for the creation of 3D biologically inspired scaffolds for e.g. tissue engineering, cosmetic or transplanting setups, with excellent functional properties and biocompatibility. This method allows to obtain very sophisticated shapes and volumes including to define pores and voids inside the structure and organize cells growth using different printing conditions or materials. This can for example be used to create holes inside the scaffold to favour the scaffold perfusion, or to favour and increase the migration of vascularization from the host inside the scaffold or to give a specific 3D shape regarding the target application. This structuring method can also be used to pattern the scaffold on existing objects, for example on microelectrode arrays, contact lenses or other medical devices. The 3D printing method is particularly adapted for printing cryogels and takes advantage of their interconnected porosity and injectability to create 3D structured objects.

In this embodiment, the invented method foresees 3D printing a multicompartment cryogel-based scaffold comprising the steps of:

a) obtaining a software-based 3D model of the three-dimensional scaffold on a computer;

b) operatively connecting said computer to a 3D printer having at least one biomaterial-based ink cartridge and a water cartridge;

c) printing a layer of the cryogel according to the software-based 3D model by dispensing the content of the cartridges on a refrigerated support kept at subzero temperature;

d) repeating step c) multiple times to obtain a stack of layers by possibly modulating the subzero temperature of the refrigerated support; and e) after an optional incubation period at subzero temperatures to complete polymerization, placing the produced cryogel at a temperature above 0° C.

the method being characterized in that each subsequent layer:

i) is deposited on the previous one after freezing of this latter;

ii) is deposited on the previous one before the complete polymerization of this latter; and iii) is deposited with a temperature higher than the freezing temperature of the previously deposited layer.

The main advantage of the present method relies in the possibility to control the pores' size by modulating the temperature of a refrigerated support on which the scaffold material is injected over time, along the support itself or even both, which in turn gives the opportunity to create a plurality of delimited compartments within the scaffold acting as physical "barriers" having for instance different cell populations/active molecules. Said temperature is typically comprised between −20° C. and −200° C., preferably between −20° C. and −80° C.

As used herein, a "compartment" is a portion of the scaffold having structural and/or mechanical features adapted to be functionally active once in use. Generally speaking, a compartment is a portion of the scaffold having a homogeneous porosity and/or a homogeneous pores' size, preferably along its entire volume. These structural features, that in turn reflect the mechanical behaviour of a compartment, translate into functional characteristics once, for instance, the scaffold is used in a tissue engineering approach in vivo, ex vivo or in vitro, as explained before. Since the additive manufacturing approach of the presently invented method exploits temperature changes to alter the porosity and/or the pores' size within the scaffold, obtaining a cryogel comprising a plurality of compartments become particularly easy and convenient. In a non-limiting, exemplary embodiment, the scaffold comprises small-pore compartments separated from large-pore compartments, wherein the ratio of average large-pore diameter to small pore diameter is of at least 2, preferably of at least 5. For example, small pore compartments can have an average pore size comprised between 10 and 50 μm, whereas a large-pore compartment can have an average pore size comprised between 150 and 250 μm.

FIG. 1 shows an exemplary approach of the printing method for creating a 3D structured scaffold made of two different materials and water as sacrificial material. The first step of the method foresees obtaining a software-based 3D model of the scaffold one wants to use. This can be taken from a database or created via a CAD software, based for instance on digitized images of portions of a subject organ or tissue obtained by e.g. non-invasive body scan. The software-based 3D model is run on a computer operatively connected with a commercially available 3D printer modified so that the printing platform carries at least two, but in some embodiments a plurality of, nozzles each connected to a cartridge used sequentially to create the different parts of the 3D scaffold. At least one cartridge comprises water or an aqueous solution and at least one cartridge comprises a biomaterial-based ink comprising for instance a natural polymeric material such as extracellular matrix-derived polymeric material, a synthetic polymeric material or combinations thereof. In one embodiment, the biomaterial-based ink does not comprise any cross-linker. Once in operation, the 3D printer starts printing the cryogel according to the software-based 3D model, wherein said cryogel is printed on a refrigerated support kept at under-zero temperature for example using Peltier systems. Indeed, for temperatures under 0° C., the cryogelation process (hydrogel polymerization at subzero temperatures, using ice crystal to define the pore space) occurs. In addition, in a preferred embodiment, the temperature of the refrigerated support of the 3D printer is controlled and regulated by the computer running the software-based 3D model of the 3D scaffold, and according to said 3D model. Since the pore dimensions depend on the temperature used for cryogelation, the temperature control allows to define parts of the object with different pores dimension, and this property can be used for instance to define adherent and non-adherent areas for cells. In one embodiment, the refrigerated support is a plate, a chamber or a reservoir.

Figure 2:
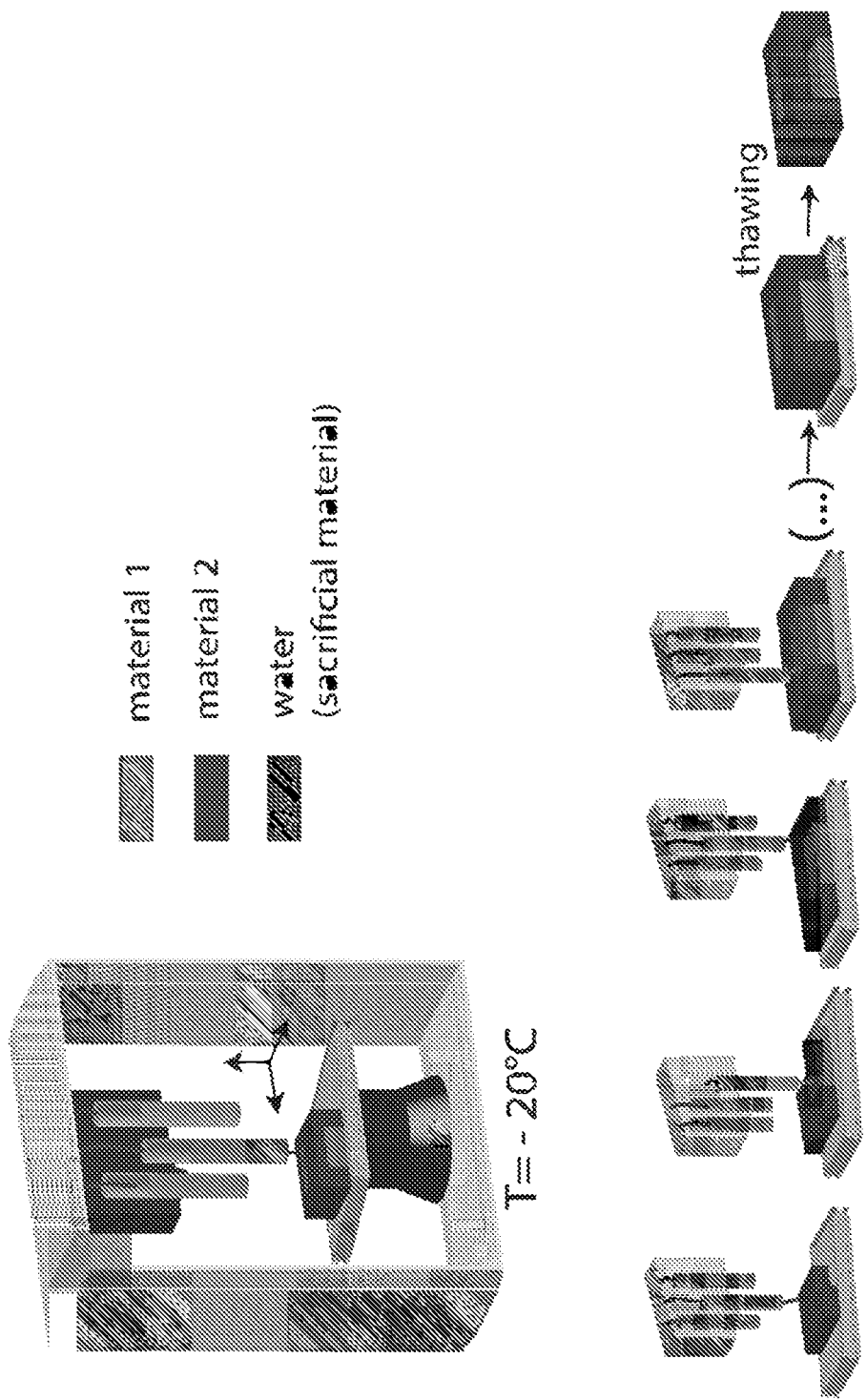
FIG. 2 shows a similar embodiment of the method of the invention using a 3D printing approach as in FIG. 1, in which the voids in the 3D scaffold are printed by using the water of a water cartridge.

In the main application, hydrogels compatible with cryogelation process such as for instance alginate, cellulose, acrylate or collagen are used to create interconnected porous areas in the 3D object. Other materials can be juxtaposed to these to define more mechanically robust areas in the 3D objects or define future void space in the 3D structure ("sacrificial materials"). These voids are structured to create for examples fluidic paths inside the scaffold or e.g. guides for tubular elements of a perfusion system to be included therein. In a preferred embodiment of the method, the voids in the 3D scaffold are printed by using the water of the water cartridge (FIG. 2). In fact, another advantage of printing cryogels is that simply water can be used as a sacrificial layer for creating 3D void spaces: by printing water at subzero temperatures, ice 3D structures are created, that will disappear upon thawing, this leaving void spaces. Other materials can be used as sacrificial materials are for instance sucrose solutions, PLGA or PLA, or even pluronics F127 as well as other materials with temperature dependent water solubility.

Figure 3:
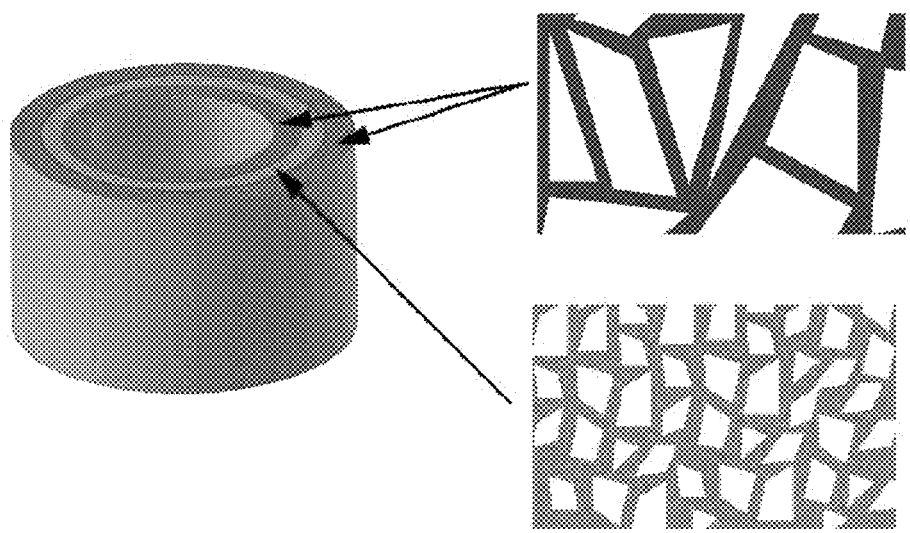
FIG. 3 depicts an exemplary cylindrical scaffold consisting of regions of cryogels with different pore sizes. The outer region, as well as the region lining the central conduit, is cryogelated for example at −20° C. and displays a mean pore size higher than the cell size. The inner region of the cylinder wall, on the other hand, is cryogelated at reduced temperatures, such as for instance −80° C., resulting in reduced pore size.

By producing different scaffold areas using different compositions or freezing temperatures, one is allowed to obtain structured 3D scaffolds with adherence contrasts for different cell types. With reference to FIG. 3, a cylindrical scaffold consisting of regions of cryogels with different pore sizes is shown. The outer region is cryogelated for example at −20° C. and displays a mean pore size higher than the cell size. The inner region, on the other hand, is cryogelated at reduced temperatures, such as for instance −80° C., resulting in reduced pore size. This area constitutes a barrier for cell penetration inside the scaffold. By seeding cells from both sides of this barrier, the repartition of different cell types in specific regions of the 3D scaffold can be organized, for instance to reproduce the epithelial/vasculature functional structure found in many metabolic internal organs such as the lung, kidney and liver.

Figure 4:
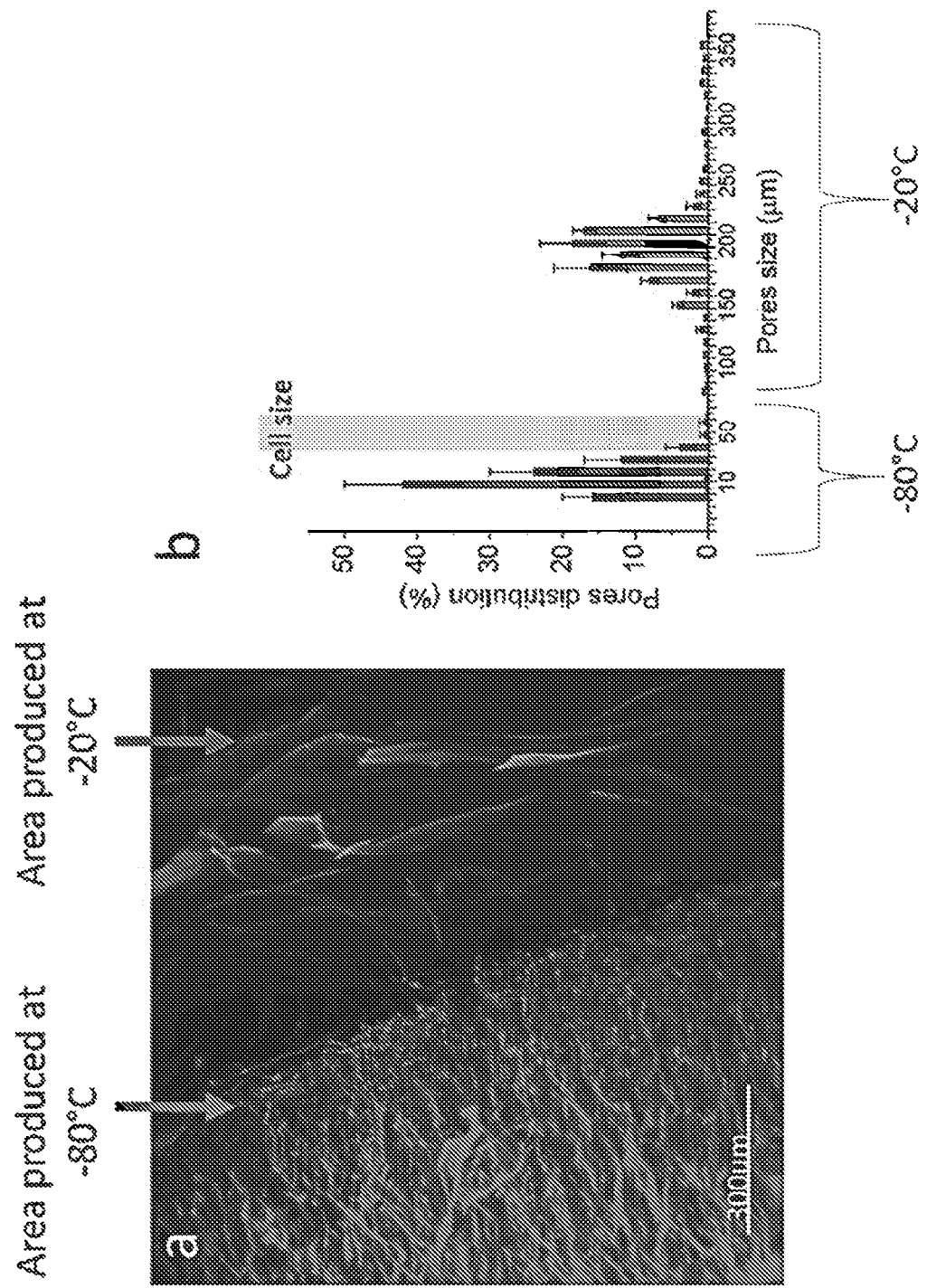
FIG. 4A shows a microscopic photograph of juxtaposed layers of hydrogel polymerized at −20° C. (right) and at −80° C. (left)
FIG. 4B shows the quantification results of the mean pores size and indication of the cell size range for the obtained cryogel.

More scaffold regions of different porosity, or with a linear change in their porosities, can be obtained by finely regulating the above described parameters, and especially the temperature of freezing. This aspect is outlined in FIG. 4A, showing juxtaposed layers of hydrogel polymerized at −20° C. (right) and at −80° C. (left). FIG. 4B shows the quantification results of the mean pores size and indication of the cell size range for the obtained cryogel. In preferred embodiments according to the invention, each layer of the biomaterial-based ink is dispensed before the partial or complete polymerization of the previous printed layer. Alternatively or additionally, non-stoichiometric binary polymerization mixtures can be used to provide function groups well beyond termination of the primary polymerization. In one embodiment, the temperature of the refrigerated support is modulated over time so that each layer defines a scaffold compartment. Alternatively or additionally, in one embodiment the temperature of the refrigerated support is modulated over time so that each layer can define more than one scaffold compartment. Alternatively or additionally, in one embodiment the temperature of the refrigerated support is modulated along the support so that each layer can define more than one scaffold compartment. These different setups allow to produce a great variety of scaffolds with tailored characteristics with a single procedure. It is understood that layers can themselves be patterned (different inks at different locations, different manufacture temperatures at different locations, places without ink, different bioactive additives or adhesion molecules at different places, inks with different freezing temperatures, inks where polymerization is already completed at the time of deposition in a gel-state, and the like). In order to obtain compartments having different structural/mechanical features, the temperature modulation of the refrigerated support can be effectuated e.g. by steps of 10° C. This can be done for example by augmenting or diminishing the temperature of the refrigerated support by steps (e.g steps of 10° C.), by continuous modulation of the temperature or using a predefined set of levels of temperatures (for instance −20° C. and −80° C.).

Some of the layers or parts of some layers maybe deposited and polymerized above their freezing temperature to provide parts with reduced porosity, and/or, depending on the chemistry used, reduced adhesion to adjacent parts.

After the fabrication step, and typically, but not necessarily, a cryo-incubation step, the cryogel scaffold is placed at a temperature above 0° C. The microscopic ice crystals in the hydrogel parts and the sacrificial macroscopic ice parts thaw and defines micro and macroscale void spaces, useful for enhancing diffusion and flows in the 3D object. For cell culture and tissue engineering applications, the microscopic void spaces are used to pattern cell diffusion inside the 3D object and its attachment or to enhance the artificial tissue vascularization, for example.

Figure 5:
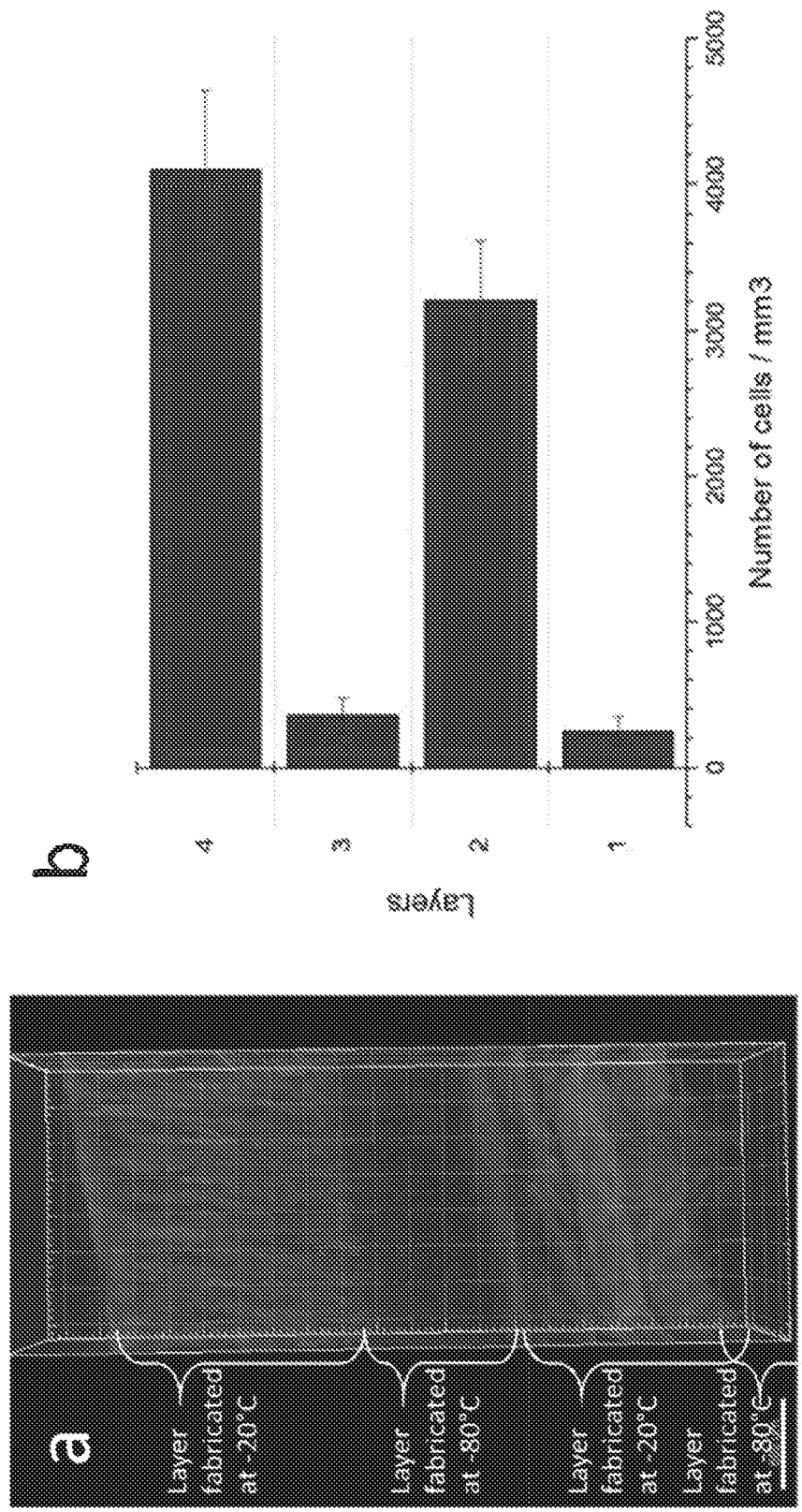
FIG. 5A shows a microscopic photograph of a multilayer, single-block scaffold of a cryogel, wherein the layers have been additively produced one on the others, and with different pores' size based on the freezing temperature chosen.
FIG. 5B shows the efficiency of the barrier activity of the compartments comprising small-sized pores, defining a quantification of the number of cells seeded on the scaffold per $mm^3$ for each layer.
Figure 9:
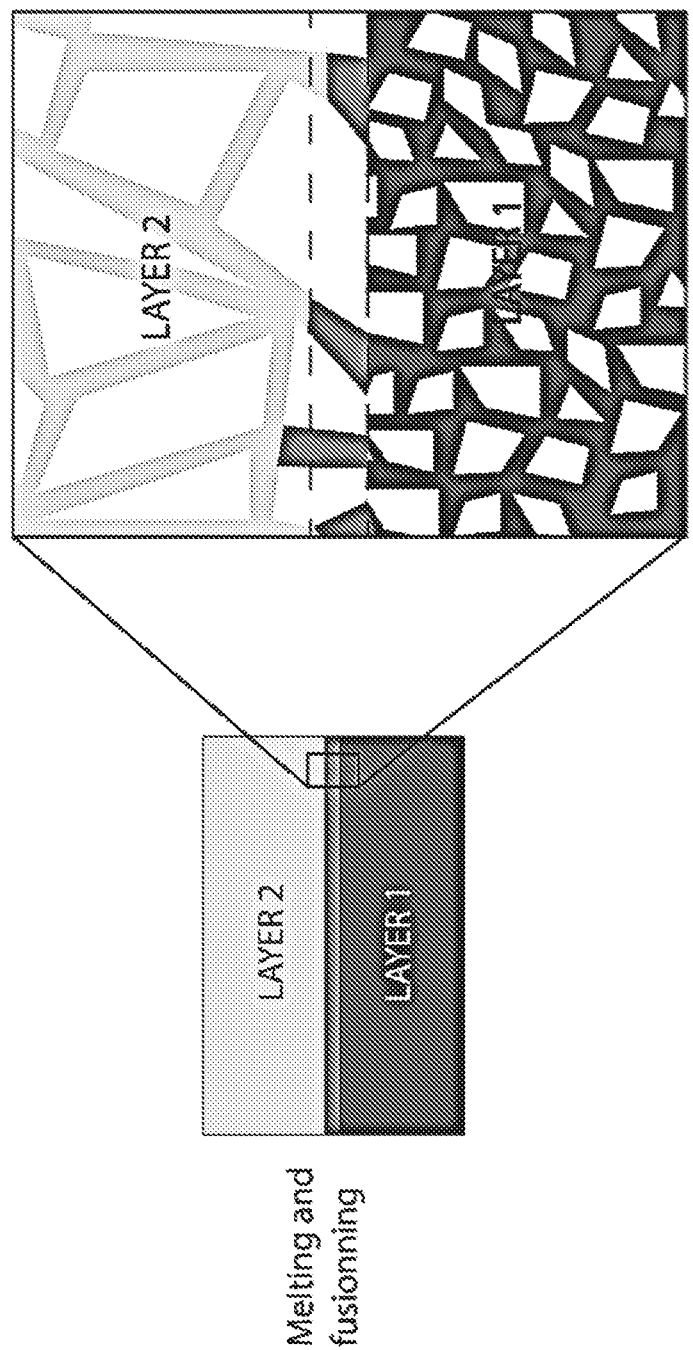
FIG. 9 shows a magnification of a cryogel scaffold according to the invention, comprising two layers separated by an in-built, intermediate thin layer that acts as a mechanically-stable junction between the polymeric cryogel layers.

As already outlined elsewhere, the present inventors, after extensive research efforts, came up with the method of the invention by taking advantage on what is absolutely peculiar in a cryogel compared to other gel solutions; actually, due to its intrinsic features and manufacturing method, the inventors realized that cryogels provide the possibility to produce solid scaffolds with functionally and mechanically different compartments with a simple additive process. In fact, when one layer or compartment is added (e.g. in a liquid form at room temperature) on another, previously produced frozen area, the former starts a local thawing process on the contact surface of the latter due to the temperature difference between the two materials, that induces a spontaneous and stable fusion between the two layers/compartments by creating an intermediate thin layer that acts as a mechanically-stable junctions between the printed layers, as depicted in FIG. 9. As exemplarily shown in FIG. 5A, several layers of a cryogel can be additively produced for instance one on the others, and with different pores' size based on the freezing temperature chosen, which is in turn tuned on the instant needs (e.g. the size of the cells that must be blocked/allowed to pass through the scaffold's compartments), giving rise to a multilayer, single-block scaffold. In an implemented embodiment, the efficiency of the barrier activity can be clearly shown (FIG. 5B), defining a quantification of the number of cells seeded on the scaffold per $mm^3$ for each layer.

As will be therefore apparent, a further object of the present invention relates to a cryogel-based multicompartment three-dimensional scaffold obtained through the developed method, characterized in that it comprises a stack of layers mechanically connected among them by a built-in, intermediate thin layer (cf. FIG. 9). Furthermore, in preferred embodiments, the obtained scaffold is characterized in that it is reversibly compressible so that it regains up to 99% of its shape after compression and release thereof within one minute. In some embodiments, the built-in, intermediate thin layer has a porosity which is smaller compared to those of adjacent compartments.

The developed scaffold addresses and solves some of the main problems of scaffold-based tissue engineering approaches, by combining at the same time advanced technologies in biomaterial production with an inventive manufacturing solution for obtaining a product which is injectable and that can provide immediate short-term bulking effect while inducing at the same time a long-term functional repair of the damaged tissues, particularly barely-accessible ones. The obtained material has optimized characteristics in terms of, inter alia, 1) compressibility and injectability, particularly needle-injectability for minimally invasive surgical procedures; and 2) biocompatibility, sterilisability and physiological adaptation to the host tissue.

For the sake of clarity, some definitions will be provided hereinafter. As used herein, a "scaffold" is any three dimensional material having a framework architecture, i.e. a support structure comprising hollow spaces within it. In preferred embodiments, a scaffold is an artificial structure capable of supporting three-dimensional body tissue/organ formation in vivo or ex vivo. In this context, a scaffold is also referred herewith as a "biomaterial" or "bioscaffold". In this embodiments, a scaffold can be considered the physical structure (including biodegradable and/or permanent materials) upon which or into which cells associate or attach. A bioscaffold allows cell attachment and migration, delivers and retains cells and biochemical factors, enables diffusion of vital cell nutrients and expressed products, exerts certain mechanical and biological influences to modify the behaviour of the cell phase and so forth.

The scaffold of the invention has been conceived and manufactured in order to act as a biocompatible, non-carcinogenic and non-immunogenic bulking agent. The general purpose was the development of a bulking formulation having improved long-term efficacy, which can stimulate host cell infiltration and integrates with the surrounding tissue once implanted in a host, thus triggering neo-tissue formation via the promotion of a bioactive environment within the application (e.g. injection) site and giving rise to long-term functional repair. In particular, the scaffold of the present invention is preferably substantially composed of a reversibly compressible gel-like material (a cryogel). Said material is usually, but not exclusively, a polymeric material suitable for creating a soft gel-like structure.

As used herein, a "polymeric material" is any material comprising polymers, large molecules (also known as macromolecules) composed of many repeated smaller units, or subunits, called monomers, tightly bonded together by covalent bonds. As used herein, the term "gel" refers to a non-fluid colloidal network or polymer network that is expanded throughout its whole volume by a fluid. A gel is a solid three-dimensional network that spans the volume of a liquid medium and ensnares it through surface tension effects. The internal network structure may result from physical bonds (physical gels) or chemical bonds (chemical gels).

In a preferred embodiment, the gel-like material is a hydrogel. As used herein, the term "hydrogel" refers to a gel in which the swelling agent is water. A hydrogel is a macromolecular polymer gel constructed of a network of cross-linked polymer chains. It is synthesized from hydrophilic monomers, sometimes found as a colloidal gel in which water is the dispersion medium. Hydrogels are highly absorbent (they can contain over 90% water) natural or synthetic polymeric networks. As a result of their characteristics, hydrogels develop typical firm yet elastic mechanical properties. Hydrogels have been used in biomedical applications, such as contact lenses and wound dressings. Among the advantages of hydrogels is that they are more biocompatible than hydrophobic elastomers and metals. This biocompatibility is largely due to the unique characteristics of hydrogels in that they are soft and contain water like the surrounding tissues and have relatively low frictional coefficients with respect to the surrounding tissues. Furthermore, hydrogels permit diffusion of aqueous compositions, and the solutes, there through, and have a high permeability to water and water-soluble substances, such as nutrients, metabolites and the like.

Several physical properties of the (hydro)gels are dependent upon concentration. Increase in (hydro)gel concentration may change the hydrogel pore radius, morphology, or its permeability to different molecular weight proteins. One skilled in the art will appreciate that the volume or dimensions (length, width, and thickness) of a hydrogel can be selected based on the user's needs, such as e.g. the region or environment into which the hydrogel is to be implanted in the frame of a surgical setting. The mechanical properties of the material can be tailored according to the application site by changing the hydrogel composition (molecular chain length, crosslinking, water content and the like).

Some non-limiting examples of suitable materials to be used for the production of the scaffold of the invention include natural polymers, such as polysaccharides, co-polymers of polysaccharides (cellulose, agarose, alginate, starch, chitosan and many others), polypeptides (silk, collagen, gelatin and many others), amelogenin or synthetic polymers such as polyurethanes, poly-olefins, polyethylene glycol (PEG), poly(glycolide) (PGA), poly(L-lactide) (PLA), carboxymethylcellulose (CMC) or poly(lactide-co-glycolide) (PLGA). The cryogel scaffold may also comprise either at least one glycosaminoglycane or at least one proteoglycane, or a mixture of those two substances. The glycosaminoglycane may be for example a hyaluronic acid, chondroitinsulfate, dermatansulfate, heparansulfate, heparine or keratansulfate. The ability to use different materials is useful in different applications and adds a further degree of versatility to the device and methods described herein. In any case, the base material is not limiting as long as the other essential mechanical requirements (e.g. pore size, pore interconnection and so forth) are met.

In order to optimize the mechanical properties of the scaffold of the invention and, in some aspects, its resorption/biodegradation rate, in preferred embodiments it is contemplated a polymer density of at least 0.1 mg/mL for the macromolecules substantially composing the polymeric material. A suitable polymer density range depends on e.g. the molecular weight of the monomer, the nature of the monomer, the crosslinking strategy and the ratio of polymers. These parameters influence the mechanical properties of the gels obtained and can be adapted depending on the applications. For example, in some embodiments of the invention the polymer content present in the used bioink can be comprised between 0.1 mg/mL and 100 mg/mL.

Concerning the degradation/resorption rate of the carrier upon in vivo application/implant in a host, this is mainly dependent on physico-chemical properties of the polymeric material of which it is composed of, as well as further factors such as crosslinking of the polymers, the polymer concentration, the site of implant into a host and the like. The degradation/resorption rate can be calibrated by adjusting said physico-chemical parameters, such as for instance by polymer crosslinking (if present), the use of inhibitor molecules, by changing the polymer density, crystallinity and/or its molecular weight distribution, changing the materials' porosity and so forth. Generally speaking, the scaffold may be, at least in part and at least in some portion thereof, intrinsically biodegradable in vivo.

As said, the scaffold is moreover highly porous. In a preferred embodiment of the invention, the pores are all interconnected in order to create a continuous net of material that can act as a plausible physical support for elements such as cells or bioactive agents, while providing at the same time additional key features to the scaffold such as its softness, low resistance to interstitial flow, high compressibility, outstanding ability to regulate the capillary pressure to a constant level over a wide range of hydration states, easiness of cell/tissue invasion and so forth. The porosity of the material is preferably comprised between 50% and 99%, allowing for evacuation of liquid from the pores upon compression.

In preferred embodiments, the pore size of the scaffold is comprised between 1 µm and 10 mm, preferably between 1 µm and 5 mm, more preferably between 1 µm and 2 mm, even more preferably between 5 µm and 500 µm. This range of pore size is particularly convenient for a scaffold material for use in tissue engineering since it is e.g. high enough to enable the growth of vessels through the porous material.

Due to the interconnections of the pores, the scaffold of the invention appears as a three-dimensionally interconnected and twisted sheet of polymeric material with an irregular shape.

Moreover, the polymer walls defining the edge of the pores of the scaffold are thin compared to the pores themselves (the pores volume/walls thickness ratio is at least 5, preferably above 10, more preferably above 20), thus providing excellent compressibility properties while preserving integrity and morphology of seeded cells throughout the compression and injection processes, if needed.

In the maximal hydration state of the scaffold, the overall polymer content is comprised between 0.1% and 10% in mass of dry polymer material, preferably between 0.5% and 3%. Upon dehydration, water is removed from the scaffold and the hydration level decreases. The progressive dehydration of the material induces an increase of the dry polymer content up to 100%. The reversible compressibility volume ratio from hydrated to dehydrated state is comprised between 1.2 and 50, preferably between 2 to 15. The reversible compressibility volume ratio from hydrated to dry state is comprised between 2 and 1000.

In the frame of the present disclosure, a "soft" material is any material that is either compressible, reversibly compressible, flexible, elastic or any combination thereof. In order to be used in living subjects, moreover, the scaffold must also imperatively be a biocompatible and/or sterilisable material suitable for medical uses.

The cryogel of the present invention can also have a shape-memory behaviour. A "shape-memory" material is a smart material that has the ability to return from a deformed state (temporary shape) due to e.g. a compression or an extension to its original (permanent) shape through an external stimulus (trigger), such as temperature change, hydration/dehydration, light pulse, electrical stimulation and the like. The shape-memory effect is not an intrinsic property, meaning that polymers do not display this effect by themselves. Shape-memory results from a combination of polymer chemistry, polymer morphology, and specific processing. By manufacturing processing, the polymer is formed into its initial, permanent shape. Afterwards, in a process called programming, the polymer sample is deformed and fixed into the temporary shape. Upon application of an external stimulus, the polymer recovers its initial, permanent shape. For instance, upon compression or dehydration, the scaffold maintains its structural integrity and shape memory properties, i.e., after compression or dehydration, the composition regains its shape after it is rehydrated or the compression forces are removed. Such a feature is particularly desirable when a minimally invasive procedure must be put in place, such as the injection of the scaffold into a subject's organ/tissue through a hollow needle. In preferred embodiments according to the invention, the obtained cryogels are able to recover up to 99% and even up to 99.9% of their initial shape upon compression (by e.g. dehydration) and subsequent release (by e.g. rehydration) very quickly, usually within one minute or less.

During or after the manufacturing process, the scaffold material can be functionalized with additional elements such as for instance bioactive molecules. Said elements can be coated on or embedded within the obtained scaffold with any suitable means known in the art, and can provide additional functional properties to the material such as enhanced/reduced biodegradation, physical stabilization, biological activity and the like. As used herein, a "bioactive molecule", as well as "(bio)active compound" or "therapeutic agent", is any active agent having an effect upon a living organism, tissue, or cell. The expression is used herein to refer to any compound or entity that alters, inhibits, activates, or otherwise affects biological or chemical events.

One skilled in the art will appreciate that a variety of bioactive compounds can be used depending upon the needs, provided, in certain embodiments, that they are compatible and not functionally impacted by the cryogelation method, the printing procedure and/or low temperature. Exemplary therapeutic agents include, but are not limited to, a small molecule, a growth factor, a protein, a peptide, an enzyme, an antibody or any derivative thereof (such as e.g. multivalent antibodies, multispecific antibodies, scFvs, bivalent or trivalent scFvs, triabodies, minibodies, nanobodies, diabodies etc.), an antigen, a nucleic acid sequence (e.g., DNA or RNA), a hormone, an anti-inflammatory agent, an anti-viral agent, an anti-bacterial agent, a cytokine, an oncogene, a tumor suppressor, a transmembrane receptor, a protein receptor, a serum protein, an adhesion molecule, a lypidic molecule, a neurotransmitter, a morphogenetic protein, a differentiation factor, an analgesic, organic molecules, metal particles, radioactive agents, polysaccharides, a matrix protein, and any functional fragment or derivative of the above, as well as any combinations thereof. For "functional fragment" is herein meant any portion of an active agent able to exert its physiological/pharmacological activity. For example, a functional fragment of an antibody could be an Fc region, an Fv region, a Fab/F(ab')/F(ab')2 region and so forth.

The bioactive compounds can be added to the scaffold material using any suitable method known in the art, such as surface absorption, physical immobilization, e.g., using a phase change to entrap the substance in the scaffold, and the like. For example, a growth factor can be mixed with the scaffold material composition while it is in an aqueous or liquid phase (e.g. within the cartridge comprising the bio-ink), and after a change in environmental conditions (e.g., pH, temperature, ion concentration), the liquid gels or solidifies, thereby entrapping the bioactive substance. Alternatively, covalent coupling, e.g., using alkylating or acylating agents, is used to provide a stable, long-term presentation of a bioactive substance on the scaffold in a defined conformation. Alternatively, non-covalent adsorbtion can be used, for example electrostatic, hydrophobic, dipole-dipole, hydrogen bonding, physisorption and the like.

The scaffolds are basically cell-free, but they can be later on seeded in vitro or in vivo with cells after their production, particularly if they are intended to transplant cells in a tissue engineering approach. Cell seeding, in its simplest implementation, involves placing the scaffold in a cell suspension and letting the cells adhere and colonize the scaffold. It is possible to greatly enhance the cell seeding process by partially dehydrating (compressing) the scaffold prior to addition of the cell suspension. In this case, the aspiration force created by the compressed scaffold's tendency to expand draws the cell suspension into the scaffold, and will seed cells deeply into the scaffold. It is further possible to use an external perfusion device (syringe pump, pressure driven flow, and the like) to induce flow across the scaffold and use this flow to efficiently seed cells deep into the scaffolds.

In all cases, the porosity and cell-adhesivity of the scaffold plays a crucial role in organizing the cell seeding. Cells of a given type will only adhere in areas which are reachable for them by fluid flow, or, on a longer term, migration, and which allow for their attachment. Areas of very low pore size (comparable to cell size and smaller) will act as a complete barrier for cell seeding by flow, be it by external perfusion or by intrinsically generated flow due to scaffold expansion. This allows to limit the areas of cell access and therefore to define function seeding compartments. Even if the pore size exceeds cell-size, areas of small pore size will act as a relative barrier since relatively more adhesion surface is available to the incoming cells.

Figure 6:
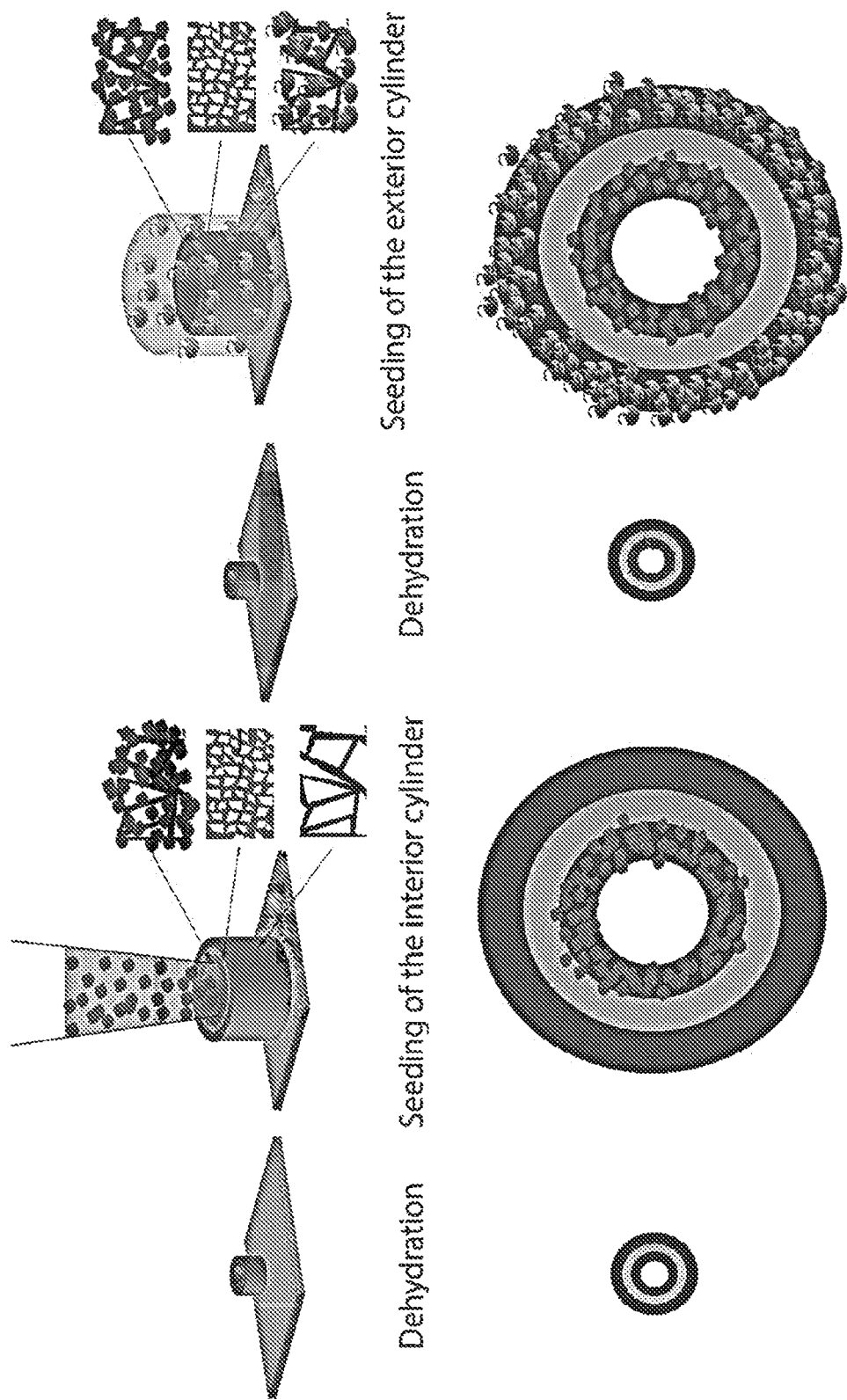
FIG. 6 schematically depicts one embodiment of the cell seeding strategies envisageable, in which a cylindrical multilayer cryogel scaffold is seeded with cells in each accessible layer sequentially.

In the presence of multiple compartments separated by small-pore barriers, different cell population can be seeded into each compartment. This is can be achieved in different configurations, for instance by pipetting or syringe injecting given cell populations into each compartment, or by externally imposed flow in different directions by using e.g. a perfusion system, as schematically shown in FIG. 6. Alternatively, stencils limiting the access to known "entry ports" for the different compartments can be used sequentially.

Further techniques such as droplet deposition of cells by inkjet printing or parallel laminar flow can be used to selectively seed compartments. Combination of techniques are also possible.

Different cell types or tissues fragments, e.g., stem vs. differentiated, and/or with various phenotypes in terms of differentiation, activation, metabolic or functional state, are optionally co-resident in the scaffold. The scaffolds are suitable for use with any cell type or tissue fragments that one may want to transplant. Such cells include but are not limited to, various stem cell populations (embryonic stem cells differentiated into various cell types), bone marrow or adipose tissue derived adult stem cells, mesenchymal stem cells, cardiac stem cells, pancreatic stem cells, neuronal cells, glial cells, spermatozoids and ovocytes, endothelial progenitor cells, outgrowth endothelial cells, dendritic cells, hematopoietic stem cells, neural stem cells, satellite cells, side population cells. Such cells may further include but are not limited to, differentiated cell populations including osteoprogenitors and osteoblasts, chondrocytes, keratinocytes for skin, intestinal epithelial cells, smooth muscle cells, cardiac muscle cells, epithelial cells, endothelial cells, urothelial cells, fibroblasts, myoblasts, chondroblasts, osteoclasts, hepatocytes, bile duct cells, pancreatic islet cells, thyroid, parathyroid, adrenal, hypothalamic, pituitary, ovarian, testicular, salivary gland cells, adipocytes and combinations thereof. For example, smooth muscle cells and endothelial cells may be employed for muscular or tubular scaffolds, e.g., scaffolds intended as vascular, esophageal, intestinal, rectal, or ureteral scaffolds; chondrocytes may be employed in cartilaginous scaffolds; cardiac muscle cells may be employed in heart scaffolds; hepatocytes and bile duct cells may be employed in liver scaffolds; myoblasts may be used in muscle regeneration; epithelial, endothelial, fibroblast, and nerve cells may be employed in scaffolds intended to function as replacements or enhancements for any of the wide variety of tissue types that contain these cells. In general, scaffolds of the invention may comprise any cell population competent to participate in regeneration, replacement or repair of a target tissue or organ, particularly barely-reachable ones such as kidneys, brain, lungs or pancreas.

The scaffold according to the invention may be prepared so that the degradation time may be controlled by using a mixture of degradable components in proportions to achieve a desired degradation rate. Alternatively, the cells themselves aid in the degradation. For example, scaffold compositions are sensitive to degradation by materials secreted by the cells themselves that are seeded within the scaffold.

Figure 7:
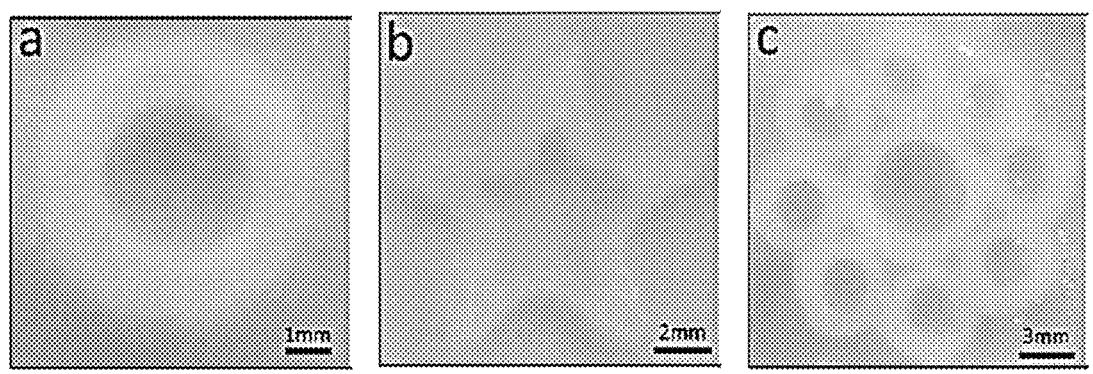
FIGS. 7A, 7B, and 7C show differently-shaped cryogel scaffolds of the invention.

The scaffold of the invention can be organized in a variety of geometric shapes (e.g., beads, pellets), niches, planar layers (e.g., thin sheets), tubes, patches, toroids and so forth (FIGS. 7A, 7B, and 7C), and can comprise in some embodiments at least two areas or compartments having different structural/functional properties. For example, multicomponent scaffolds are constructed in e.g. concentric layers, each of which is characterized by different physico-chemical properties (% polymer, % crosslinking of polymer, chemical composition of scaffold, pore size and/or architecture, porosity, presence or different concentration of bioactive agents and so on). Each niche can host one or more cell populations and have a specific effect on them, e.g., promoting or inhibiting a specific cellular function, proliferation, differentiation, migration and so forth. Cells incubated in the scaffold can be for instance induced to differentiate or migrate out of the scaffold to directly affect a target tissue, e.g., and injured tissue site. Such a configuration is particularly useful in maintaining for long time periods the "stemness" of a population of cells, while simultaneously pushing daughter cells to multiply rapidly and differentiate appropriately for participation in tissue regeneration.

Figure 8:
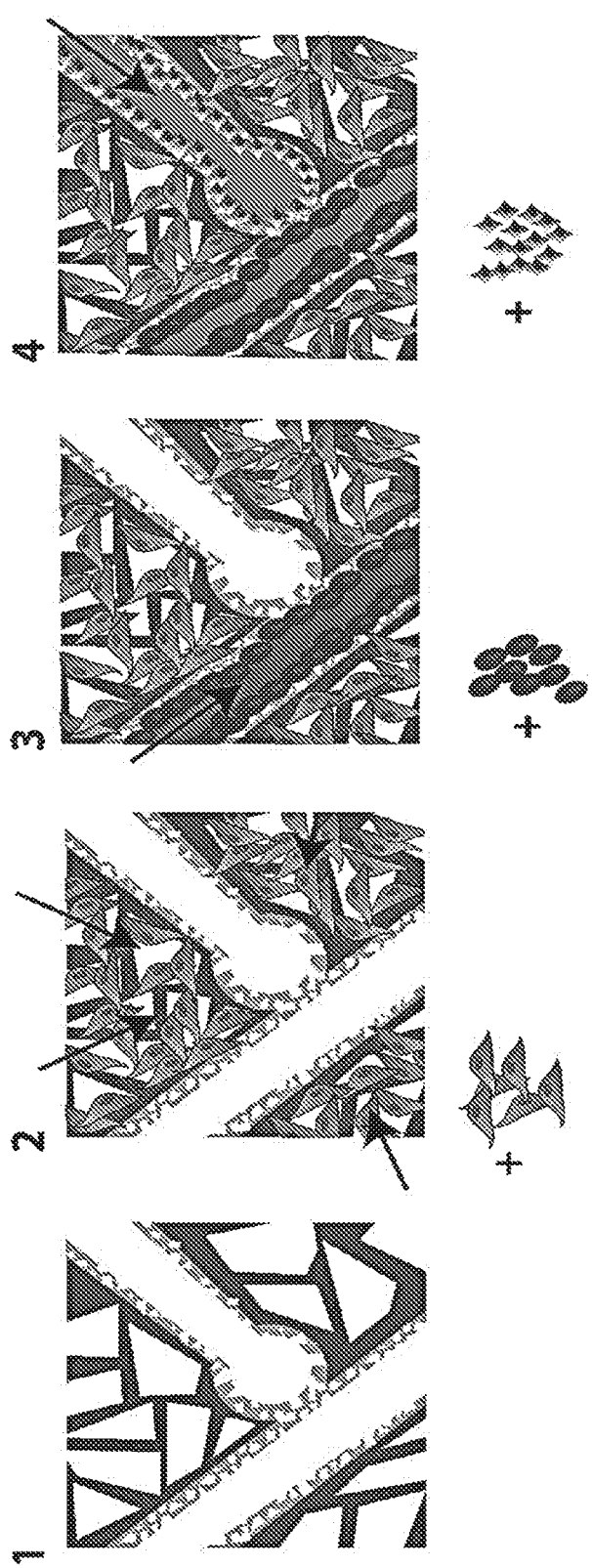
FIG. 8 depicts a design strategy for the cryogel scaffold of the invention, in which a number of compartments or areas or perfusion pathways are present. Compartment-specific cell seeding is enabled by the contrast of cell-permeant and cell-non-permeant (small-pore) areas. In each compartment thus separated, upon seeding by perfusion or aspiration, a defined and a priori distinct cell population is therefore established.

The compartmentalization and functionalization of the scaffold can be obtained by rational design and fabrication processes using different compositions or concentrations of compositions for each compartment. For example, a stem cell population can be encapsulated within the scaffold, using standard encapsulation techniques. Alternatively or additionally, two different areas or compartments can be formed within the bioscaffold from the same material that contains distinct factors (e.g., morphogens, growth factors, adhesion ligands), the same material in a distinct form (e.g., varying mechanical properties or porosity), or a completely different material that provides appropriate chemical/physical properties. The scaffold can be designed to have a number of compartments or areas in which cells enter in parallel and distribute according to their characteristics (e.g., size or mobility), serially pass through all or some of the compartments, or a combination of both. The different compartments can even be construed to induce distinct fates for the contained cells during the passage therein (FIG. 8).

For example, scaffolds may include networks of channels and/or other structures that allow for nutrients to be supplied to cells and for waste material to be removed from cells on the scaffold in the form of perfusion pathways. A "perfusion pathway" is a set of one or more confined or partially confined passages configured and arranged to guide flow of a fluid (liquids or gases) within and/or on a scaffold. In some embodiments, a perfusion pathway is in fluid communication (e.g., fluidically connected) with one or more inlets through which a fluid is supplied to the perfusion pathway. In some embodiments, a perfusion pathway is in fluid communication (e.g., fluidically connected) with one or more outlets through which a fluid exits the perfusion pathway. Different perfusion pathways having different configurations and properties can be used to control the distribution pattern and timing of different materials to a scaffold (FIG. 8). Moreover, fluids can enter, flow through and/or exit one or more perfusion pathway by simple diffusion or through a force imparted by the atmospheric pressure.

Moreover, the scaffold can be differentially permeable, allowing cell displacement only in certain physical areas of the scaffold. The permeability of the scaffold composition is regulated, for example, by selecting or engineering a material for greater or smaller pore size, density, polymer crosslinking, stiffness, toughness, ductility, and/or viscoelasticity.

Turning back again to cryogels, this particular kind of hydrogels provides further advantages in terms of bioscaffold manufacturing. In hydrogels, pore size plays a role in the adherence of cells to the scaffold and in their penetration inside the same. If the mean pore size is higher than the cell size, cells can penetrate inside the interconnected pores network and adhere to the gel fibers, whereas if the mean pore size is smaller than the cell size, cells cannot penetrate inside the scaffold. This contrast of pore size can be used to create an organization of cells inside the 3D scaffold. The mean pore size inside cryogel scaffolds can be easily controlled by different parameters, including the temperature of freezing while polymerization, wherein lower temperatures lead to reduced pore size, the pre-polymer composition or the incubation time after initiation of crosslinking, but prior to the gel production. The present inventors observed that all these parameters must be studied, adapted and even dynamically regulated so that the congelation starts before the gel polymerization in order for the scaffold to have its key features.

A number of organs present a microscopic organization with a functional, locally 2D epithelial compartment, and a vascular compartment ensuring blood supply. Major examples of this organizations are the lung, the liver, and the kidney. The apical surface of the epithelium is in contact with channels connected to the outside world (i.e. alveola and airways for the lung, bile ducts for the liver, and tubules and ultimately the urinary tract for the kidney), while the basal part of the epithelial cells resides on the vascular structures. Reproducing this general type of organization is possible when using the 3D structuration technique of the present disclosure. For instance, a cell-impermeant barrier needs to be fabricated between two compartments, and the two compartments seeded with one cell population, or even two different cell types (or mixtures of cell types). The overall porous nature of the structure allows for efficient seeding of the two different cell supply, each in its compartment, but against the small-pore interface.

The scaffold can be ideally transplanted on or close to a target tissue, introduced into or onto a bodily tissue/organ using a variety of methods and tools known in the art, preferably via minimally invasive surgical devices and procedures that envisage an injection step by using catheters, cannulas or preferably syringe needles.

The invention claimed is:

1. A method of producing a cryogel-based multicompartment three-dimensional scaffold, said method comprising steps of:
   a) depositing a first liquid comprising a first precursor of a first polymeric material to form a first frozen polymeric layer on a refrigerated support kept below 0° C. temperature;
   b) repeatedly depositing a second liquid comprising a second precursor of a second polymeric material to form a plurality of subsequent polymeric layers on the refrigerated support at below 0° C., said first frozen polymeric layer and said plurality of subsequent polymeric layers forming a stack of polymeric layers, wherein step (b) further comprises polymerizing the first and/or second precursor, wherein the first precursor and the second precursor are the same or different; and
   c) bringing the stack of polymeric layers formed in step b) to a temperature above 0° C.;
   wherein following step (c), the stack comprises a crosslinked polymer matrix in one or more of the polymeric layers having pores with a mean pore size between 1 µm and 500 µm,
   wherein each of the plurality of subsequent layers is:
   i) deposited on a previously deposited layer after freezing of said previously deposited layer;

ii) deposited on said previously deposited layer before complete polymerization of said previously deposited layer; and iii) deposited at a temperature higher than a freezing temperature of said previously deposited layer.

2. The method according to claim 1, further comprising: incubating the stack of polymeric layers at a below 0° C. temperature.

3. The method of claim 1, wherein step b) is performed by any one or a combination of casting and molding, 3D printing, screen printing, and photopolymerization of at least a liquid precursor of at least a polymeric material.

4. The method of claim 3, wherein step b) is performed by 3D printing.

5. The method of 4, wherein the temperature of the refrigerated support of the 3D printer is controlled and regulated by the computer running the software-based 3D model of the 3D scaffold, and according to said 3D model.

6. The method according to claim 1, wherein the temperature of the refrigerated support is modulated over time so that each polymeric layer in the stack defines one or more than one scaffold compartment.

7. The method according to claim 1, wherein the temperature of the refrigerated support is modulated along the refrigerated support such that each polymeric layer in the stack defines more than one scaffold compartment.

8. The method according to claim 1, wherein the temperature of the refrigerated support is kept between the freezing point of the polymeric material and absolute zero.

9. The method according to claim 1, wherein the temperature of the refrigerated support is kept between 0° C. and −200° C.

10. The method according to claim 1, wherein the temperature of the refrigerated support is kept between −20° C. and −80° C.

11. A cryogel-based multicompartment three-dimensional scaffold produced by the method of claim 1, wherein the stack of layers that comprise the cryogel-based multicompartment three-dimensional scaffold are mechanically connected by a built-in intermediate layer, having a thickness smaller than those of its adjacent layers.

12. The scaffold of claim 11, wherein the cryogel-based multicompartment three-dimensional scaffold has a network of interconnected pores with a porosity comprised between 50% and 99%.

13. The scaffold of claim 11, wherein the cryogel-based multicompartment three-dimensional scaffold comprises small-pore compartments separated from large-pore compartments, and wherein a ratio of average large-pore diameter to small pore diameter is at least 2.

14. The scaffold of claim 11, wherein the cryogel-based multicompartment three-dimensional scaffold comprises small-pore compartments separated from large-pore compartments, and wherein a ratio of average large-pore diameter to small pore diameter is at least 5.

15. The scaffold of claim 12, wherein pore volume divided by wall thickness of pores in the scaffold is at least 5.

16. The scaffold of claim 12, wherein pore volume divided by wall thickness of pores in the scaffold is at least 10.

17. The scaffold of 11, wherein the cryogel-based multicompartment three-dimensional scaffold is flowable and injectable through a syringe needle.

18. The scaffold of claim 11, wherein cryogel-based multicompartment three-dimensional scaffold comprises an active compound therein and/or thereon.

* * * * *